United States Patent [19]
Goto et al.

[11] Patent Number: 5,641,725
[45] Date of Patent: Jun. 24, 1997

[54] SULPHONYLAMINOPHENYLURACIL HERBICIDES FOR PADDY FIELD

[75] Inventors: Toshio Goto, Shimotsuga-gun; Seishi Ito, Oyama; Chieko Ueno, Oyama; Tatsuya Yamaoka, Oyama; Kazuhiro Ukawa, Oyama; Natsuko Minegishi, Oyama, all of Japan

[73] Assignee: Nihon Bayer Agrochem K.K., Tokyo, Japan

[21] Appl. No.: 562,923

[22] Filed: Nov. 27, 1995

[30] Foreign Application Priority Data

Dec. 2, 1994 [JP] Japan ................... 6-323952

[51] Int. Cl.⁶ .................................. A01N 43/54
[52] U.S. Cl. ..................... 504/134; 504/136; 504/243
[58] Field of Search ................... 504/136, 243, 504/134

[56] References Cited

U.S. PATENT DOCUMENTS 5,084,084 1/1992 Satow et al. .................. 71/92
5,154,755 10/1992 Satow et al. .................. 71/92

FOREIGN PATENT DOCUMENTS 4412079 2/1995 Germany .

*Primary Examiner*—S. Mark Clardy
*Attorney, Agent, or Firm*—Sprung Horn Kramer & Woods

[57] ABSTRACT

A herbicide for paddy field comprising sulphonylaminophenyluracil derivative as an active ingredient which is represented by the formula (I):

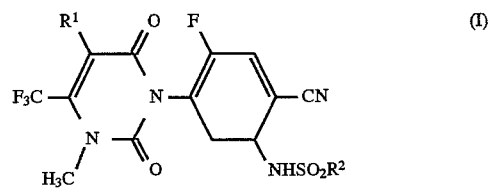

wherein $R^1$ represents hydrogen or methyl, $R^2$ represents $C_{1-5}$alkyl, fluro-substituted $C_{1-2}$alkyl or $C^{3-6}$cycloalkyl, optionally applied in combination with another herbicide.

13 Claims, No Drawings

SULPHONYLAMINOPHENYLURACIL HERBICIDES FOR PADDY FIELD

The present invention relates to new herbicides for paddy field applications. More specifically, the invention relates to herbicides for paddy field using phenyluracils as active ingredients, and mixed herbicides of phenyluracil derivatives with one or more other herbicidal compounds.

It is already known that some phenyluracil derivatives show herbidical properties. (See: Japanese Patent Kokai Publication Hei 3-204865). However, it is unknown that sulphonylaminophenyluracils can be used as herbicides for paddy field applications.

Substituted sulphonylaminophenyluracils of the general formula (I)

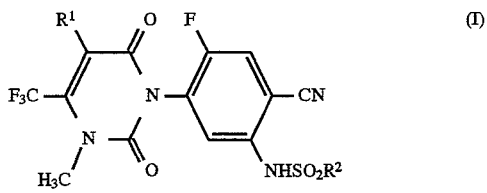

have been found,
wherein
R$^1$ represents hydrogen or methyl, and
R$^2$ represents C$_{1-5}$alkyl, fluoro-substituted C$_{1-2}$ alkyl or C$_{3-6}$ cycloalkyl,
showing excellent herbicidal activities for paddy field applications.

Some phenyluracil derivatives of the above formula (I) are specifically disclosed in Japanese Kokai Publication Hei 3-204865 but it does not teach or suggest the application of sulphonylaminophenyluracils of the general formula (I) as herbicides for paddy field applications.

Surprisingly, the substituted sulphonylaminophenyluraciles of the general formula (I) exhibit a considerably improved herbicidal activity but do not show phytotoxicity to rice plants in paddy fields. The sulphonylaminophenyluracils of the general formula (I) show very strong herbicidal activities on lowland weeds, such as *Monochoria vaginalis* Presl, *Cyperus serotinus* Rottb., *Sagittaria pygmaea* Miq., and annual broad-leaved weeds such as, *Lindernia procumbens* Borbas, *Rotala indica* Koehne (Indian toothcup), *Elatine triandra* Schk., *Ammannia multiflora* Roxb., and *Dopatrium iunceum* Hamilt. (dopatrium).

Furthermore, according to the present invention, mixed herbidical compositions which contain sulphonylaminophenyluracils of the general formula (I) and at least one known herbidical compound which is selected from the group listed below have been found to exhibit very strong herbicidal effects on lowland weeds.

The group of the herbicidal compounds consists of: acetamide herbicides, chloroacetanilide herbicides, thiolcarbamate herbicides, azole herbicides, pyrimidine herbicides, sulphonylurea herbicides, pyrazole herbidices, propionanilide herbicides, phenoxypropionic acid ester herbicides, benzylurea herbidices, phenoxycarboxylic acid herbicides and triazinc herbicides.

Unexpectedly, the mixed herbicidal compositions of the present invention have excellent herbicidal effects on such kinds of weeds where neither the sulphonylaminophenyluracil derivatives of the general formula (I) nor those herbicides which are listed above show sufficient activity when used alone. In other words, the effect of the blended herbicidal compositions of the present invention substantially exceeds the additional effect of the individual active ingredients which constitute the compositions. Because of such synergistic herbicidal activities, the substituted sulphonylaminophenylureacils as well as the mixed herbicidal compositions show excellent herbicidal properties such as broad herbicidal spectrum and perform well even with longer times between successive applications. For example, on application in paddy framing, the substituted sulphonylaminophenylureacils as well as the mixed herbicidal compositions show very good herbicidal effects on the weeds which emerge on various growth stages of paddy rice plants from the initial emergence just after rice transplantation to the vegetative period, and has long durability excellent residual activity, and no phytotoxicity to rice plants.

Preferred compounds of the sulphonylaminophenyluracils of the general formula (I) which are used alone or mixed in herbicidal compositions as herbicides for paddy fields, are those wherein R$^1$ represents hydrogen or methyl, and R$^2$ represents C$_{1-4}$ alkyl, difluoromethyl, trifluoromethyl, cyclopropyl, cyclopentyl or cyclohexyl. Especially preferred sulphonylaminophenyluracils of the general formula (I) are those wherein R$^1$ represents hydrogen or methyl, and
R$^2$ represents C$_{1-3}$ alkyl, trifluoromethyl or cyclopropyl.

Individually, and apart from the compounds listed in the preparation examples, the following sulphonylaminophenyluracils of the general formula (I) may be mentioned:

1-(4-cyano-2-fluoro-5-methylsulphonylaminophenyl)-3,6-dihydro-2,6-dioxo-3-methyl-4-trifluormethyl-1(2H)-pyrimidine, 1-(4-cyano-2-fluoro-5-ethylsulphonylaminophenyl)-3,6-dihydro-2,6-dioxo-3-methyl-4-trifluoromethyl-1(2H)-pyrimidine, 1-(4-cyano-2-fluoro-5-n-propylsulphonylaminophenyl)-3,6-dihydro-2,6-methyl-4-trifluoromethyl-1(2H)-pyrimidine, 1-(4-cyano-2-fluoro-5-isopropylsulphonylaminophenyl)-3,6-dihydro-2,6-dioxo-3-methyl-4-trifluoromethyl-1(2H)-pyrimidine, 1-(4-cyano-2-fluoro-5-cyclopropylsulphonylaminophenyl)-3,6-dihydro-2,6-dioxo-3-methyl-4-trifluoromethyl-1(2H)-pyrimidine, 1-(4-cyano-2-fluoro-5-n-butylsulphonylaminophenyl)-3,6-dihydro-2,6-dioxo-3-methyl-4-trifluoromethyl-1(2H)-pyrimidine, 1-(4-cyano-2-fluoro-5-methylsulphonylaminophenyl)-3,6-dihydro-2,6-dioxo-3,5-dimethyl-4-trifluoromethyl-1(2H)-pyrimidine, 1-(4-cyano-2-fluoro-5-ethylsulphonylaminophenyl)-3,6-dihydro-2,6-dioxo-3,5-dimethyl-4-trifluoromethyl-1(2H)-pyrimidine, 1-(4-cyano-2-fluoro-5-n-propylsulphonylaminophenyl)-3,6-dihydro-2,6-dioxo-3,5-dimethyl-4-trifluoromethyl-1(2H)-pyrimidine, 1-(4-cyano-2-fluoro-5-isopropylsulphonylaminophenyl)-3,6-dihydro-2,6-dioxo-3,5-dimethyl-4-trifluoromethyl-1-(2H)-pyrimidine, 1-(4-cyano-2-fluoro-5-trifluoromethylsulphonylaminophenyl)-3,6-dihydro-2,6-dioxo-3,5-dimethyl-4-trifluoromethyl-1(2H)-pyrimidine, 1-(4-cyano-2-fluoro-5-trifluoromethylsulphonylaminophenyl)-3,6-dihydro-2,6-dioxo-3-methyl-4-trifluoromethyl-1(2H)-pyrimidine, and 1-(4-cyano-2-fluoro-5-difluoromethylsulphonylaminophenyl)-3,6-dihydro-2,6-dioxo-3,5-dimethyl-4-trifluoromethyl-1(2H)-pyrimidine.

The sulphonylaminophenyluracil derivatives of the general formula (I) which are represented by the above-listed group of compounds can be obtained by the method which is described, for example, in German Patent Application No. 4327743 and No. 4412079.

Representative sulphonylaminophenyluracil derivatives of the general formula (I) and their physicochemical properties include:

(I)-1:
1-(4-cyano-2-fluoro-5-methylsulphonylaminophenyl)-3,6-dihydro-2,6-dioxo-3-methyl-4-trifluoromethyl-1(2H)-pyrimidine, m.p. 192° C.;

(I)-2:
1-(4-cyano-2-fluoro-5-ethylsulphonylaminophenyl)-3,6-dihydro-2,6-dioxo-3-methyl-4-trifluoromethyl-1(2H)-pyrimidine, m.p. 172° C.;

(I)-3:
Triethylamine salt of 1-(4-cyano-2-fluoro-5-ethylsulphonylaminophenyl)-3,6-dihydro-2,6-dioxo-3-methyl-4-trifluoromethyl-1(2H)-pyrimidine, m.p. 41° C.;

(I)-4:
1-(4-cyano-2-fluoro-5-n-propylsulphonylaminophenyl)-3,6-dihydro-2,6-dioxo-3-methyl-4-trifluoromethyl-1(2H)-pyrimidine, m.p. 142° C.;

(I)-5:
1-(4-cyano-2-fluoro-5-isopropylsulphonylaminophenyl)-3,6-dihydro-2,6-dioxo-3-methyl-4-trifluoromethyl-1(2H)-pyrimidine, m.p. 161° C.;

(I)-6:
1-(4-cyano-2-fluoro-5-cyclopropylsulphonylaminophenyl)-3,6-dihydro-2,6-dioxo-3-methyl-4-trifluoromethyl-1(2H)-pyrimidine, m.p. 180° C.;

(I)-7:
1-(4-cyano-2-fluoro-5-n-butylsulphonylaminophenyl)-3,6-dihydro-2,6-dioxo-methyl-4-trifluoromethyl-1(2H)-pyrimidine, m.p. 155° C.; and (I)-8:
1-(4-cyano-2-fluoro-5-methylsulphonylaminophenyl)-3,6-dihydro-2,6-dioxo-3,5-dimethyl-4-trifluoromethyl-1(2H)-pyrimidine, m.p. 242° C.

Specific examples of the herbicidal compounds which are used with the sulphonylaminophenyluracil derivatives of the general formula (I) in the mixed herbicidal compositions of the present invention are as follows:

acetamide herbicides:
2-benzothiazol-2-yloxy-N-methylacetanilide,
(RS)-2-brom-N-(α,α-dimethylbenzyl)-3,3-dimethylbutylamide, chloroacetanilide herbicides:
2-chloro-2',6'-diethyl-N-(2-propoxyethyl) acetanilide,
2-chloro-2',6'-diethyl-N-(butoxymethyl)acetanilide,
2-chloro-N-(3-methoxy-2-thienyl)-2',6'-dimethylacetanilide, thiolcarbamate herbicides:
S-(4-chlorobenzyl)-N,N-diethylthiocarbamate,
S-benzyl-1,2-dimethylpropyl(ethyl)thiocarbamate,
O-3-tert.-butylphenyl-6-methoxy-2-pyridyl(methyl)thiocarbamate,
S-ethylhexahydro-1H-azepine-1-carbothioate, azole herbicides:
1-(diethylcarbamoyl)-3-(2,4,6-trimethylphenylsulfonyl)-1,2,4-thiazole,
1-(3-chloro-4-trifluoromethylphenyl)-4-(N,N-dimethylcarbamoyl)-5(4H)-tetrazolinone,
1-(3-chloro-4-trifluoromethylthiophenyl)-4-(N,N-dipropylcarbamoyl)-5(4H)-tetrazolinone,
1-(3-chloro-4-trifluoromethoxyphenyl)-4-(N,N-dipropylcarbamoyl)-5(4H)-tetrazolinone,
1-(3-chloro-4-isopropylphenyl)-4-(N,N-diethylcarbamoyl)-5(4H)-tetrazolinone,
1-(3-chloro-4-isopropylphenyl)-4-(N,N-dipropylcarbamoyl)-5(4H)-tetrazolinone,
1-(3-chloro-4-isopropylphenyl)-4-(N,N-diallylcarbamoyl)-5(4H)-tetrazolinone,
1-(2-chlorophenyl)-4-(N,N-diethylcarbamoyl)-5(4H)-tetrazolinone,
1-(2-chlorophenyl)-4-(N,N-dipropylcarbamoyl)-5(4H)-tetrazolinone,
1-(2-chloro-6-methylphenyl)-4-(N,N-diethylcarbamoyl)-5(4H)-tetrazolinone,
1-(2,6-dichlorophenyl)-4-(N,N-diethylcarbamoyl)-5(4H)-tetrazolinone,
1-(2-chloro-6-methylphenyl)-4-(N-ethyl-N-isopropylcarbamoyl)-5(4H)-tetrazolinone,
1-(2-chloro-6-methylphenyl)-4-(N,N-dipropylcarbamoyl)-5(4H)-tetrazolinone,
1-(2-chlorophenyl)-4-(N-cyclopentyl-N-ethylcarbamoyl)-5(4H)-tetrazolinone,
1-(2-chlorophenyl)-4-(N-cyclopentyl-N-propylcarbamoyl)-5(4H)-tetrazolinone,
1-(2-chlorophenyl)-4(N-cyclohexyl-N-ethylcarbamoyl)-5(4H)-tetrazolinone,
1-(2-chloro-6-methylphenyl)-4-(N-cyclopentyl-N-propylcarbamoyl)-5(4H)-tetrazolinone,
1-(2-bromophenyl)-4-(N-cyclopentyl-N-ethylcarbamoyl)-5(4H)-tetrazolinone,
1-(2-bromophenyl)-4-(N-cyclopentyl-N-propylcarbamoyl)-5(4H)-tetrazolinone,
1-(2-bromo-6-methylphenyl)-4-(N-cyclopentyl-N-propylcarbamoyl)-5(4H)-tetrazolinone, pyrimidine herbicides:
methyl 2-[(4,6-dimethoxy-2-pyrimidinyl)oxy]-6-[1-methoxyimino)ethyl]-benzoate, sulphonylurea herbicides:
methyl α-(4,6-dimethoxypyrimidin-2-yl-carbamoylsulfamoyl)-O-toluate,
ethyl 5-(4,6-dimethoxypyrimidin-2-yl-carbamoylsulfamoyl)-1-methylpyrazol-4-carboxylate,
N-(2-chloroimidazole[1,2-a]pyridin-3-yl-sulphonyl)-N'-(4,6-dimethoxy-2-pyrimidinyl)urea,
N-((4,6-dimethoxypyrimidin-2-yl)aminocarbonyl)-1-methyl-4-(2-methyl-2H-tetrazol-5-yl)-1H-pyrazol-5-sulphonamide,
N-[[4,6-dimethoxy-1,3,5-triazin-2-yl)amino]carbonyl]-2-(2-methoxyethoxy)benzenesulphonamide,
1-[[o-(cyclopropylcarbonyl)phenyl]sulfamoyl-3-(4,6-dimethoxy-2-pyrimdinyl)urea, pyrazole herbicides:
4-(2,4-dichlorobenzoyl)-1,3-dimethylpyrazol-5-yl-p-toluenesulfonate,
2-[4-(2,4-dichloro-m-toluyl)-1,3-dimethylpyrazol-5-yloxy]-4-methylacetophenone,
2-[4-(2,4-dichlorobenzoyl)-1,3-dimethylpyrazol-5-yloxy]acetophenone, propionanilide herbicides:
2-(β-naphthyloxy)propionanilide,
(RS)-2-(2,4-dichloro-m-tolyloxy)propionanilide, phenoxypropionic acid ester herbicides:

n-butyl(R)-2-[4-(2-fluoro-4-cyanophenoxy)phenoxy]
propionate,
benzylurea herbicides:
1-(α,α-dimethylbenzyl)-3-p-tolylurea,
N-[(2-chlorophenyl)methyl]-N'-(1-methyl-1-phenylethyl)urea,
phenoxycarboxylic herbicides:
2-methyl-4-chlorophenoxybutyric acid,
2,4-dichlorophenoxyacetic acid,
triazine herbicides:
2,4-bis(ethylamino)-6-methylthio-1,3,5-triazine,
2-ethylamino-4-(1,2-dimethylpropylamino)-6-methylthio-1,3,5-triazine.

The above compounds per se are known and described, for example, in Japanese Patent Kokai Publications Sho 46-14077, Sho 54-36648, Sho 56-28885, Sho 56-43455, Sho 61-16395, Hei 2-7562, Hei 5-46344; U.S. Pat. No. 5,009,699; EP-A 435 170, Japanese Patent Kokai Publications Sho 57-56452, Sho 57-72903, Sho 57-112379, Sho 57-171904, Sho 59-122488, Hei 1-38091, Hei 1-66156, Hei 2-233665, Hei 5-331153, hei 5-331154, Hei 5-339249, Hei 6-199818, Hei 6-306061; Pesticide Manual, 1991 (9th ed.) (The British Crop Protect Council), Pesticide Handbook, 1992 (Japan Plant-Epidemic Prevention Association), etc.

In accordance with the present invention, the weight ratio of each active ingredient in the mixed herbicidal compositions is not strictly restricted, but can be varied over relatively wide ranges depending on the individual application period, etc. Generally, the weight ratios of the sulphonylaminophenyluraci's of the general formula (I) to the herbicidal compound or compounds in the mixture ranges from one part by weight of a sulphonylaminophenyluracil of the general formula (I) to about 2 to about 300 parts, preferably about 20 to about 150 parts of acetamide herbicidal compound, about 1 to about 100 parts, preferably about 5 to about 50 parts of chloroacetanilide herbicidal compound, about 3 to about 400 parts, preferably about 5 to about 300 parts of thiolcarbamate herbicidal compound, about 0.5 to about 100 parts, preferably about 2 to about 80 parts of azole herbicidal compound, about 0.005 to about 20 parts, preferably about 0.1 to about 10 parts of pyrimidine herbicidal compound, about 0.02 to 60 parts, preferably about 0.03 to about 30 parts sulphonylurea herbicidal compound, about 3 to about 200 parts, preferably about 4 to about 120 parts of pyrazole herbicidal compound, about 7.5 to about 400 parts, preferably about 10 to about 320 parts of propionanilide herbicidal compound, about 0.2 to about 60, preferably about 0.3 to about 40 parts of phenoxypropionic acid ester herbicidal compound, about 1 to about 400 parts, preferably about 3 to about 300 parts of benzylurea herbicidal compound, about 0.2 to about 100 parts, preferably about 1 to about 80 parts of phenoxycarboxylic acid herbicidal compound, and about 0.05 to about 120 parts, preferably about 0.1 to about 100 parts of triazine herbicidal compound, or a weighted average thereof.

The herbicide and mixed herbicidal compositions according to the present invention exhibit very strong herbicidal effects on lowland weeds, and good compatibility with paddy rice. Therefore, they are suitable for use as selective herbicides and selective mixed herbicidal compositions in paddy fields.

The herbicide and mixed herbicide compositions according to the present invention can be used to control the following lowland weeds:
Dicotyledon weeds of the genera:
Polygonum, Rorippa, Rotala, Lindernia, Bidens, Dopartrium, Eclipta, Elatine, Gratiola, Vandellia, Ludwigia, Oenanthe, Ranunculus and Deinostema.
Monocotyledon weeds of the genera:
Echinochloa, Panicum, Poa, Cyperus, Monochoria, Fimbristylis, Sagittaria, Eleocharis, Scirpus, Alisma, Aneilema, Blyxa, Eriocaulon and Potamogeton.
More concrete examples of the lowland weeds are:
scientific name (plant name)
Dicotyledon weeds
  *Rotala indica* Koehne (Indian toothcup)
  *Lindernia procumbens* Philcox (common falsepimpernel)
  *Ludwigia prostrata* Roxburgh (false loosestrife)
  *Potamogeton distinctus* A. Benn (bod pondweed)
  *Elatine triandra* Schk (long stemmed water wort)
  *Oenanthe javanica* (dropwort)
Monocotyledon weeds
  *Echinochloa oryzicola* vasing (barnyardgrass)
  *Monochoria vaginalis* Presl (monochoria)
  *Eleocharis acicularis* L. (cow hairs)
  *Eleocharis kuroguwai* Ohwi (water chestnut)
  *Cyperus difformis* L. (small flower)
  *Cyperus serotinus* Rottboel (water nutgrass)
  *Sagittaria pygmaea* Miq (Japanese ribbon wapato)
  *Alisma canaliculatum* A. Br. et Bouche (narrow-leaved arrowhead)
  *Scirpus juncoides* Roxburgh (bulrush).

The herbicide and mixed herbicidal compositions of the present invention can be converted to the customary formulations, such as solutions, emulsions, wettable powders, suspensions, powders, soluble powders, dusting agents, granules, suspension-emulsion concentrates, very fine capsules in polymeric substances, natural and synthetic materials impregnated with the active compounds, etc.

These formulations are produced in a known manner, for example, by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can be used as auxiliary solvents. As liquid solvents, there are suitable in the main: aromatic hydrocarbons, such as xylene, toluene or alkyl naphthalenes; chlorinated aromatic hydrocarbons and chlorinated aliphatic hydrocarbons; such as chloribenzenes, chloroethylenes or methylene chloride; aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone; strongly polar solvents, such as dimethylformamide and dimethylsulphoxide; as well as water.

As solid carriers there are suitable: for example, ammonium salts and ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn and tobacco stalks.

As emulsifying and/or foam-forming agents there are suitable: for example non-ionic and anionic emulsifiers, such as polyoxyethylene-fatty acid esters, polyoxyethylene-fatty alcohols ethers, for example alkylaryl polyglycol ethers, alkylsulphonates, alkylsulphates, arylsulphonates as well as albumin hydrolysis products.

As dispersing agents there are suitable: for example lignin-sulphite waste liquors and methylcellulose.

Adhesives may also be used optionally in formulations such as powders, granules, natural and synthetic materials impregnated with active compound or emulsions, and the followings are to be mentioned as examples of such adhesives: for example carboxymethylcellulose and natural and synthetic polymers such as gum arabic, polyvinyl alcohol and polyvinyl acetate, as well as natural phospholipids, such as cephalins and lecithins, synthetic phospholipids. As further additives there are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trance nutrients such as salts of metals, for example, iron, manganese, boron, copper, molybdenum and zinc.

The formulations in general contain between 0.1 and 95% by weight preferably between 0.5 and 90% by weight of the compound of formula (I) or mixture of the compound of formula (I) and other herbicidal compounds as active compounds.

The mixed herbicidal compositions of the invention can be used for controlling of weeds as they are or as formulations and can be mixed with any known herbicides. The mixture may be either prepared in advance in the form of a final formulation or prepared by tank-mixing immediately before use.

Furthermore, the herbicides and the herbicidal compositions of the invention can be used by mixing with any other known agricultural active compound which can be used in paddy fields such as a fungicide, bactericide, insecticide, plant growth regulator, nutrition agent, soil improvement agent, other herbicides, etc.

In order to apply the herbicides and the herbicidal compositions according to the present invention, the active compounds can be used alone or in the form of formulations or in other forms suitable for application, such as ready-to-use solutions, emulsions, suspensions, powders, wettable powders, soluble powders, granules, by adjusting and diluting the formulations. They may be applied by any conventional methods such as watering, atomizing, powder spreading or granule scattering.

The active compound and the herbicidal compositions according to the present invention may be applied at any stage from preemergence or postemergence, and also they may be suitably applied before, at, or after rice-transplanting.

The amount applied of the active compounds and the herbicidal compositions according to the invention is not strictly limited and may be varied within a wide range depending on the desired effect, the location of application, the time of application, weather and climate and the like, and when the sulphonylaminophenyluracil derivatives of the general formula (I) are used as active compounds, the application rate may vary from about 0.005 kg/ha to about 0.5 kg/ha, preferably from about 0.01 kg/ha to about 0.2 kg/ha of the active compound. When herbicidal compositions which contain the sulphonylaminophenyluracil derivatives of the general formula (I) and other herbicidal compound or compounds as active compounds are used, the total amount of such other active ingredient can be from about 0.01 kg/ha to $^2$ kg/ha, preferably from about 0.02 kg/ha to about 1.7 kg/ha, with the proviso that the amount can be varied corresponding to the condition of growth of the lowland weeds to be controlled, growth stage of the paddy, and natural conditions of the field to be treated, including the atmospheric temperature, temperature at the water surface of the paddy field, and soil conditions, etc.

The following examples illustrate the excellent effects of the herbicides and mix herbicidal compositions of the invention. It will be understood that the specification and examples are illustrative but not limitative of the present invention and that other embodiments within the spirit and scope of the invention will suggest themselves to those skilled in the art. In the examples, parts are by weight unless otherwise noted.

EXAMPLES

Test Example 1

Test of herbicidal effect on lowland weeds
Applied compounds (active compounds)
(I)-2, (I)-4, (I)-8 (as previously defined) as the sulphonylaminophenyluracil derivatives.
As other herbicidal compounds:

(II)-1:
  2-benzothiazol-2-yloxy-N-methylacetanilide,
(II)-2:
  (RS)-2-bromo-N-($\alpha,\alpha$-dimethylbenzyl)-3,3-dimethylbutylamide,
(III)-1:
  2-chloro-2',6'-diethyl-N-(2-propoxyethyl)acetanilide,
(III)-2:
  2-chloro-2',6'-diethyl-N-(butoxymethyl)acetanilide,
(IV)-1:
  S-(4-chlorobenzyl)-N,N-diethylthiocarbamate,
(IV)-2:
  S-benzyl-1,2-dimethylpropyl(ethyl)thiocarbamate,
(IV)-3:
  O-3-tert-butylphenyl 6-methoxy-2-pyridyl(methyl)thiocarbamate,
(V)-1:
  1-(diethylcarbamoyl)-3-(2,4,6-trimethylphenylsulphonyl)-1,2,4-thiazole,
(V)-2:
  1-(3-chloro-4-trifluoromethylphenyl)-4-(N,N-dimethylcarbamoyl)-5(4H)-tetrazolinone,
(V)-3:
  1-(3-chloro-4-trifluoromethoxyphenyl)-4-(N,N-dipropylcarbamoyl)-5(4H)-tetrazolinone,
(V)-4:
  1-(3-chloro-4-isopropylphenyl)-4-(N,N-dipropylcarbamoyl)-5(4H)-tetrazolinone,
(V)-5:
  1-(2-chlorophenyl)-4-(N,N-dipropylcarbamoyl)-5(4H)-tetrazolinone,
(V)-6:
  1-(2-chloro-6-methylphenyl)-4-(N,N-diethylcarbamoyl)-5(4H)-tetrazolinone,
(V)-7:
  1-(2-chloro-6-methylphenyl)-4-(N,N-dipropylcarbamoyl)-5(4H)-tetrazolinone,
(V)-8:
  1-(2-chlorophenyl)-4-(N-cyclopentyl-N-ethylcarbamoyl)-5(4H)-tetrazolinone, (V)-9:
  1-(2-chlorophenyl)-4-(N-cyclopentyl-N-propylcarbamoyl)-5(4H)-tetrazolinone, (V)-10:
  1-(2-chlorophenyl)-4-(N-cyclohexyl-N-ethylcarbamoyl)-5(4H)-tetrazolinone, (V)-11:
  1-(2-chloro-6-methylphenyl)-4-(N-cyclopentyl-N-propylcarbamoyl)-5(4H)-tetrazolinone, (V)-12:
  1-(2-bromophenyl)-4-(N-cyclopentyl-N-ethylcarbamoyl)-5(4H)-tetrazolinone, (VI):
  methyl 2-[(4,6-dimethoxy-2-pyrimidinyl)oxy]-6-[1-methoxyimino)ethyl]-benzoate, (VII)-1:
  methyl α-(4,6-dimethoxypyrimidin-2-yl-carbamoylsulfamoyl)-O-toluate, (VII)-2:
  ethyl 5-(4,6-dimethoxypyrimidin-2-yl-carbamoylsulfamoyl)-1-methylpyrazol-4-carboxylate, (VII)-3:
  N-(2-chloroimidazole[1,2-a]pyridin-3-yl-sulfonyl)-N'-(4,6-dimethoxy-2-pyrimidinyl)urea, (VIII)-1:
  4-(2,4-dichlorobenzoyl)-1,3-dimethylpyrazol-5-yl-p-toluenesulfonate, (VIII)-2:
  2-[4-(2,4-dichloro-m-toluoyl)-1,3-dimethylpyrazol-5-yloxy]-acetophenone, (IX)-2:
  2-(β-naphthyloxy)propionanilide, (X):
  n-butyl(R)-2-[4-(2-fluoro-4-cyanophenoxy)phenoxy] propionate.

Preparation of formulations:

carrier: xylene 5 parts emulsifier: benzyloxy polyglycol ether 1 part

A part of one of the active compounds and the above amounts of carrier and emulsifier are mixed to obtain an emulsion. A prescribed amount of this emulsion is diluted with water to be subjected to the test below.

Testing procedure:

Each 3 seedlings of paddy rice (cultivar: Nipponbare) of 2.5 leafstage (15 cm tall) were transplanted in two places in 1/2000 are large pot (25×20×9 cm) filled with paddy field soil. Then seeds of barnyardgrass, cow hairs, bulrush, monochoria, broad-leaved weeds (common falsepimpernel, Indian toothcup, long stemmed water wort, Ammannia mul-tiflora Roxb. Dopatrium junceum Hammilt), water nutgrass, and Japanese ribbon wapato were sowed, and water was poured on the soil to a depth of 2–3 cm. A prescribed amount of the above active compound and the mixed active compounds as the effective ingredient were applied to the surface of the water 5 days after the transplantating of the paddy rice in each test pot.

The herbicidal effects on weeds and rice plants were examined on the day after 3 weeks from the herbicidal treatment during which period the water depth of 3 cm was maintained. the herbicidal effect was rated as 100% in the case of complete death and as 0% in the case where equivalent weed growth was observed as in untreated test pots. The present damage to the rice plants.

The species and symbols of the weeds are as follows:

$W_1$: barnyardgrass $W_2$: cow hair $W_3$: bulrush $W_4$: monochoria $W_5$: broad-leaved weeds $W_6$: water nutgrass $W_7$: Japanese ribbon wapato Below-identified compounds were used as a control.

C-1:

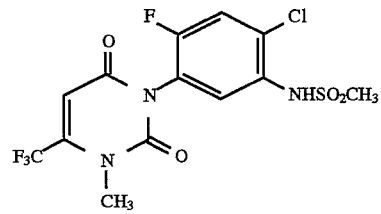

C-2:

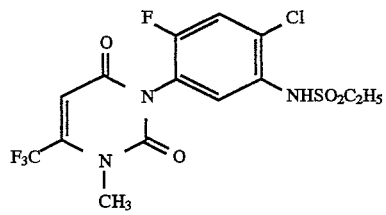

C-3:

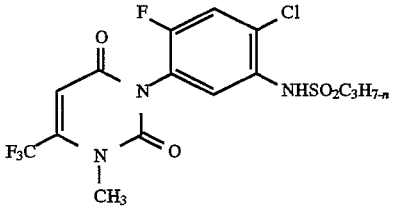

The results are indicated in Table 1 and Table 2.

TABLE 1

| compound No. | amount of active ingredient g/ha | herbicidal effect on weeds | | | | | | | damage to rice |
|---|---|---|---|---|---|---|---|---|---|
| | | $W_1$ | $W_2$ | $W_3$ | $W_4$ | $W_5$ | $W_6$ | $W_7$ | |
| (I)-2 | 12 | 30 | 80 | 80 | 100 | 100 | 90 | 90 | 0 |
| (I)-4 | 12 | 20 | 80 | 80 | 100 | 100 | 90 | 90 | 0 |
| (I)-8 | 20 | 30 | 90 | 95 | 100 | 100 | 95 | 95 | 0 |
| | 40 | 40 | 90 | 100 | 100 | 100 | 100 | 100 | 0 |

TABLE 1-continued

| compound No. | amount of active ingredient g/ha | herbicidal effect on weeds | | | | | | | damage to rice |
|---|---|---|---|---|---|---|---|---|---|
| | | W₁ | W₂ | W₃ | W₄ | W₅ | W₆ | W₇ | |
| comparative | | | | | | | | | |
| C-1 | 12 | 40 | 90 | 80 | 100 | 100 | 60 | 70 | 40 |
| C-2 | 12 | 30 | 80 | 80 | 100 | 100 | 40 | 60 | 40 |
| C-3 | 12 | 30 | 80 | 70 | 100 | 100 | 40 | 40 | 20 |

TABLE 2

| compound No. | amount of active ingredient g/ha | herbicidal effect on weeds | | | | | | | damage to rice |
|---|---|---|---|---|---|---|---|---|---|
| | | W₁ | W₂ | W₃ | W₄ | W₅ | W₆ | W₇ | |
| (I)-2 + (II)-1 | 8 + 500 | 100 | 100 | 100 | 100 | 100 | 95 | 90 | 0 |
| (I)-4 + (II)-1 | 8 + 500 | 100 | 100 | 100 | 100 | 100 | 90 | 90 | 0 |
| (I)-4 + (II)-1 | 8 + 1000 | 100 | 100 | 100 | 100 | 100 | 100 | 100 | 0 |
| (I)-2 + (III)-1 | 8 + 250 | 100 | 100 | 100 | 100 | 100 | 100 | 90 | 0 |
| (I)-4 + (III)-1 | 8 + 250 | 100 | 100 | 100 | 100 | 100 | 100 | 90 | 0 |
| (I)-4 + (III)-2 | 8 + 250 | 100 | 100 | 100 | 100 | 100 | 100 | 90 | 0 |
| (I)-2 + (IV)-1 | 8 + 1000 | 100 | 100 | 100 | 100 | 100 | 100 | 95 | 0 |
| (I)-4 + (IV)-2 | 8 + 1200 | 100 | 100 | 100 | 100 | 100 | 95 | 90 | 0 |
| (I)-8 + (IV)-3 | 15 + 600 | 100 | 100 | 95 | 100 | 100 | 95 | 90 | 0 |
| (I)-2 + (V)-2 | 8 + 150 | 100 | 100 | 100 | 100 | 100 | 98 | 98 | 0 |
| (I)-4 + (V)-1 | 8 + 150 | 100 | 98 | 100 | 100 | 100 | 100 | 95 | 0 |
| (I)-4 + (V)-5 | 8 + 150 | 100 | 100 | 100 | 100 | 100 | 100 | 90 | 0 |
| (I)-8 + (V)-9 | 15 + 100 | 100 | 100 | 100 | 100 | 100 | 100 | 100 | 0 |
| (I)-8 + (V)-10 | 15 + 100 | 100 | 100 | 100 | 100 | 100 | 100 | 100 | 0 |
| (I)-8 + (V)-6 | 15 + 150 | 100 | 100 | 95 | 100 | 100 | 100 | 90 | 0 |
| (I)-2 + (V)-3 | 8 + 150 | 100 | 100 | 95 | 100 | 100 | 100 | 95 | 0 |
| (I)-2 + (V)-12 | 8 + 100 | 100 | 100 | 95 | 100 | 100 | 95 | 95 | 0 |
| (I)-2 + (V)-7 | 8 + 150 | 100 | 100 | 100 | 100 | 100 | 98 | 95 | 0 |
| (I)-4 + (V)-8 | 8 + 100 | 100 | 100 | 95 | 100 | 100 | 100 | 90 | 0 |
| (I)-8 + (V)-11 | 15 + 100 | 100 | 100 | 95 | 100 | 100 | 100 | 95 | 0 |
| (I)-8 + (V)-4 | 15 + 150 | 100 | 100 | 90 | 100 | 100 | 95 | 90 | 0 |
| (I)-2 + (V)-12 | 8 + 150 | 100 | 100 | 100 | 100 | 100 | 98 | 95 | 0 |
| (I)-8 + (VI) | 15 + 15 | 100 | 100 | 100 | 100 | 100 | 100 | 95 | 0 |
| (I)-2 + (VII)-1 | 8 + 30 | 100 | 100 | 100 | 100 | 100 | 100 | 100 | 0 |
| (I)-4 + (VII)-2 | 8 + 15 | 100 | 100 | 100 | 100 | 100 | 100 | 95 | 0 |
| (I)-8 + (VII)-3 | 8 + 45 | 100 | 100 | 100 | 100 | 100 | 100 | 100 | 0 |
| (I)-2 + (VIII)-1 | 8 + 500 | 90 | 100 | 100 | 100 | 100 | 90 | 100 | 0 |
| (I)-4 + (VIII)-2 | 8 + 500 | 95 | 100 | 100 | 100 | 100 | 90 | 100 | 0 |
| (I)-4 + (IX)-1 | 8 + 1200 | 90 | 100 | 100 | 100 | 100 | 95 | 100 | 0 |
| (I)-8 + (X) | 30 + 150 | 100 | 98 | 100 | 100 | 100 | 100 | 100 | 0 |
| (I)-2 | 8 | 30 | 80 | 70 | 100 | 100 | 90 | 80 | 0 |
| (I)-4 | 8 | 20 | 80 | 80 | 100 | 100 | 90 | 80 | 0 |
| (I)-8 | 15 | 20 | 90 | 100 | 100 | 90 | 90 | 95 | 0 |
| (I)-8 | 30 | 30 | 90 | 100 | 100 | 100 | 100 | 100 | 0 |
| (II)-1 | 500 | 100 | 90 | 90 | 100 | 40 | 40 | 0 | 0 |
| (II)-2 | 1000 | 50 | 70 | 95 | 100 | 70 | 80 | 70 | 0 |
| (III)-1 | 250 | 100 | 90 | 100 | 100 | 95 | 70 | 10 | 0 |
| (III)-2 | 250 | 100 | 90 | 100 | 100 | 95 | 60 | 10 | 0 |
| (IV)-1 | 1000 | 90 | 80 | 80 | 90 | 70 | 70 | 0 | 0 |
| (IV)-2 | 1200 | 90 | 70 | 80 | 90 | 70 | 60 | 0 | 0 |
| (IV)-3 | 600 | 80 | 60 | 10 | 70 | 60 | 20 | 0 | 0 |
| (V)-1 | 125 | 98 | 60 | 100 | 100 | 95 | 70 | 40 | 5 |
| (V)-2 | 150 | 80 | 70 | 60 | 90 | 90 | 40 | 20 | 0 |
| (V)-3 | 150 | 70 | 70 | 60 | 90 | 90 | 40 | 10 | 0 |
| (V)-4 | 150 | 70 | 70 | 70 | 90 | 90 | 40 | 10 | 0 |
| (V)-5 | 150 | 80 | 80 | 70 | 90 | 70 | 30 | 20 | 0 |
| (V)-6 | 150 | 80 | 80 | 90 | 90 | 70 | 30 | 20 | 0 |
| (V)-7 | 150 | 80 | 90 | 80 | 90 | 70 | 40 | 20 | 0 |
| (V)-8 | 100 | 80 | 70 | 60 | 80 | 80 | 50 | 20 | 0 |
| (V)-9 | 100 | 70 | 70 | 70 | 80 | 90 | 50 | 10 | 0 |
| (V)-10 | 100 | 80 | 80 | 70 | 80 | 90 | 60 | 20 | 0 |
| (V)-11 | 100 | 70 | 70 | 70 | 90 | 80 | 60 | 20 | 0 |
| (V)-12 | 100 | 80 | 80 | 70 | 80 | 90 | 50 | 20 | 0 |
| (VI) | 15 | 100 | 20 | 50 | 90 | 40 | 0 | 20 | 0 |
| (VII)-1 | 30 | 50 | 70 | 90 | 100 | 100 | 80 | 70 | 0 |
| (VII)-2 | 15 | 60 | 60 | 90 | 100 | 100 | 80 | 80 | 0 |
| (VIII)-1 | 500 | 40 | 60 | 70 | 100 | 100 | 40 | 90 | 0 |

TABLE 2-continued

| compound No. | amount of active ingredient g/ha | herbicidal effect on weeds | | | | | | | damage to rice |
|---|---|---|---|---|---|---|---|---|---|
| | | $W_1$ | $W_2$ | $W_3$ | $W_4$ | $W_5$ | $W_6$ | $W_7$ | |
| (VIII)-2 | 500 | 50 | 60 | 70 | 100 | 100 | 50 | 90 | 0 |
| (IX)-1 | 1200 | 70 | 70 | 80 | 90 | 90 | 50 | 80 | 0 |
| (X) | 150 | 100 | 0 | 0 | 0 | 0 | 0 | 0 | 0 |

Formulation Example 1

(granule)

25 Parts of water is added to a mixture of the following ingredients and the mixture is thoroughly kneaded, granulated in an extrusion granulator, and dried to provide a granule formulation.

(I)-2 10 parts bentonite 30 parts talc 58 parts lingnin sulfonate 2 parts.

Formulation Example 2

(wettable powder)

Water is added to a mixture of the following ingredients. The mixture is extruded through a 0.3 mm mesh screen and dried to provide the wettable powder.

(I)-8 20 parts bentonite 15 parts calcined diatomaceous earth powder 35 parts sodium lignin sulfonate 30 parts.

Formulation Example 3

(granule)

Granules are obtained by the procedure described in the formulation Example 1 using the following ingredients:

(I)-2 0.5 part (II)-1 10 parts bentonite 30 parts talc 57.5 parts lignin sulfonate 2 parts.

It will be understood that the specification and examples are illustrative but not limitative of the present invention and that other embodiments within the spirit and scope of the invention will suggest themselves to those skilled in the art.

What is claimed is:

1. A method for combating weeds in the paddy field cultivation of a crop, said method comprising applying to said field an amount effective to combat such weeds of at least one (A) sulphonyl phenyl aminouracil of the formula (Ia):

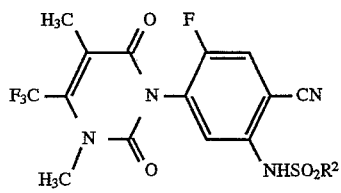

wherein $R^2$ represents methyl or ethyl.

2. The method according to claim 1, wherein (A) is 1-(4-cyano-2-fluoro-5-methylsulphonylaminophenyl)-3,6-dihydro-2,6-dioxo-3,5-dimethyl-4-trifluoromethyl-1(2H)-pyrimidine.

3. The method according to claim 1, wherein the paddy field in the absence of said sulphonylaminophenyluracil contains lowland weeds.

4. The method according to claim 3, wherein the weeds comprise at least one of

Dictyledon weed of the genera:

Polygonum, Rorippa, Rotala, Lindernia, Bidens, Dopartrium, Eclipta, Elatine, Gratiola, Vandellia, Ludwigia, Oenanthe, Ranunculus and Deinostems, and a Monocotyleden weed of the genera:

Echinochloa, Paniciaum, Poa, Cyperus, Monochoria, Fimbristylis, Sagittaria, Eleocharis, Scirpus, Alisma, Aneilema, Blyxa, Ericaulon, and Potamogeton.

5. The method according to claim 2, wherein the paddy field in the absence of said sulphonylaminophenyluracil contains at least one weed selected from the group consisting of a Dictyledon weed of the genera:

Polgonum, Rorippa, Rotala, Lindernia, Bidens, Dopartrium, Eclipta, Elatine, Gratiola, Vandellia, Ludwigia, Oenanthe, Ranunculus and Deinostems, and a Monocotyleden weed of the genera:

Echinochloa, Paniciaum, Poa, Cyperus, Monochoria, Fimbristylis, Sagittaria, Eleocharis, Scirpus, Alisma, Aneilema, Blyxa, Ericaulon, and Potamogeton.

6. The method according to claim 1, wherein in addition to (A) at least one sulphonylaminophenyluracil of the formula (Ia), there is also applied (B) a synergistically effective amount of at least one of about 2 to about 300 parts of an acetamide herbicidal compound, about 1 to about 100 parts of a chloroacetanilide herbicidal compound, about 3 to about 400 parts of a thiolcarbamate herbicidal compound, about 0.5 to about 100 parts of an azole herbicidal compound, about 0.005 to about 20 parts of a pyrimidine herbicidal compounds, about 0.02 to about 60 parts of a sulphonylurea herbicidal compound, about 3 to about 200 parts of a pyrazole herbicidal compound, about 7.5 to about 400 parts of a proplonanilide herbicidal compound, about 0.2 to about 60 of a phenoxypropionic acid ester herbicidal compound, about 1 to about 400 parts of a benzylurea herbicidal compound, about 0.2 to about 100 parts of phenoxycarboxylic acid herbicidal compound, and about 0.05 to about 120 parts of a triazine herbicidal compound or a weighted mixture thereof.

7. The method according to claim 6, wherein the herbicidal compound (B) comprises at least one compound selected from the group consisting of 2-benzothiazol-2-yloxy-N-methylacetanilide, (RS)-2-bromo-N-(α,α-dimethylbenzyl)-3,3-dimethylbutylamide, 2-chloro-2',6'-diethyl-N-(2-propoxyethyl)acetanilide, 2-chloro-2',6'-diethyl-N-(butoxymethyl)acetanilide, 2-chloro-N-(3-methoxy-2-thienyl)-2',6'-dimethylacetanilide, S-(4-chlorobenzyl)-N,N-diethylthiocarbamate, S-benzyl-1,2-dimethylpropyl(ethyl)thiocarbamate, O-3-tert-butylphenyl 6-methoxy-2-pyridyl-(methyl)thiocarbamate, S-ethylhexahyde-1H-azepin-1-carbothioate, 1-(diethylcarbamoyl)-3-(2,4,6-trimethylphenylsulfonyl)-1,2,4-thiazole, 1-(3-chloro-4-trifluoromethylphenyl)-4-(N,N-dimethylcarbamoyl)-5(4H)-tetrazolinone, 1-(3-chloro-4-trifluoromethylthiophenyl)-4-(N,N-dipropylcarbamoyl)-5(4H)-tetrazolinone, 1-(3-chloro-4-trifluoromethyoxyphenyl)-4-(N,N-dipropylcarbamoyl)-5(4H)-tetrazolinone, 1-(3-chloro-4-isopropylphenyl)-4-(N,N-diethylcarbamoyl)-5(4H)-tetrazolinone, 1-(3-chloro-4-isopropylphenyl)-4-(N,N-dipropylcarbamoyl)-5(4H)-tetrazolinone, 1-(3-chloro-4-isopropylphenyl)-4-(N,N-diallylcarbamoyl)-5(4H)-tetrazolinone, 1-(2-chlorophenyl)-4-(N,N-diethylcarbamoyl)-5(4H)-tetrazolinone, 1-(2-chlorophenyl)-4-(N,N-dipropylcarbamoyl)-5(4H)-tetrazolinone, 1-(2-chloro-6-methylphenyl)-4-(N,N-diethylcarbamoyl)-5(4H)-tetrazolinone, 1-(2,6-dichlorophenyl)-4-(N,N-diethylcarbamoyl)-5(4H)-tetrazolinone, 1-(2-chloro-6-methylphenyl)-4-(N-ethyl-N-isopropyl)-5(4H)-tetrazolinone, 1-(2-chloro-6-methylphenyl)-4-(N,N-dipropylcarbamoyl)-5(4H)-tetrazolinone, 1-(2-chlorophenyl)-4-(N-cyclopentyl-N-ethylcarbamoyl)-5(4H)-tetrazolinone, 1-(2-chlorophenyl)-4-(N-cyclopentyl-N-propylcarbamoyl)-5(4H)-tetrazolinone, 1-(2-chlorophenyl)-4-(N-cyclohexyl-N-ethylcarbamoyl)-5(4H)-tetrazolinone, 1-(2-chloro-6-methylphenyl)-4-(N-cyclopentyl-N-propylcarbamoyl)-5(4H)-tetrazolinone, 1-(2-bromophenyl)-4-N-(N-cyclopentyl-N-ethylcarbamoyl)-5(4H)-tetrazolinone, 1-(2-bromophenyl)-4-(N-cyclopentyl-N-propylcarbamoyl)-5(4H)-tetrazolinone, 1-(2-bromo-6-methylphenyl)-4-(N-cyclopentyl-N-propylcarbamoyl)-5(4H)-tetrazolinone, methyl 2[4,6-dimethoxy-2-pyrimidinyl)oxy]-6-[1-methoxyimino)ethyl]-benzoate, methyl α-(4,6-dimethoxypyrimidin-2-yl-carbamoylsulfamoyl)-O-toluate, ethyl 5-(4,6-dimethoxypyrimidin-2-yl-carbamoylsulfamoyl)-1-methylpyrazol-4-carboxylate, N-(2-chloroimidazole[1,2-a]pyridin-3-yl-sulfonyl)-N'-(4,6-dimethoxy-2-pyrimidinyl)urea, N-(4,6-dimethoxypyrimidin-2-yl)aminocarbonyl)-1-methyl-4-(2-methyl-2H-tetrazole-5-yl)-1H-pyrazol-5-sulfonamide, N-[[4,6-dimethoxy-1,3,5-triazine-2-yl)amino]carbonyl]-2-(2-methoxyethoxy)benzenesulfonamide, 1-[[o-cyclopropylcarbonyl)phenyl]sulfamoyl-3-(4,6-dimethoxy-2-pyrimidinyl)urea, 4-(2,4-dichlorobenzoyl)-1,3-dimethylpyrazol-5-yl-p-toluenesulfonate, 2-[4-(2,4-dichloro-m-toluoyl)-1,3-dimethylpyrazol-5-yloxy]-4-methylacetophenone, 2-[4-(2,4-dichlorobenzoyl)-1,3-dimethylpyrazol-5-yloxy]acetophenone, 2-(β-naphthyl-oxy)propionanilide, (RS)-2-(2,4-dichloro-m-tolyloxy)propionanilide, n-butyl(R)-2-[4-(2-fluoro-4-cyanophenoxy)phenoxy]propionate, 1-(α,α-dimethylbenzyl)-3-p-tolylurea, N-[(2-chlorophenyl)methyl]-N'-(1-methyl-1-phenylethyl) urea, 2-methyl-4-chlorophenoxybutyric acid, 2,4-dichlorophenoxyacetic acid, 2,4-bis(ethylamino)-6-methylthio-1,3,5-triazine and 2-ethylamino-4-(1,2-dimethylpropylamino)-6-methylthio-1,3,5-triazine.

8. The method according to claim 6, wherein (A) per one part by weight of the sulphonylaminophenyluracil, there is applied (B) a synergistically effective amount of at least one of
about 2 to about 300 parts of an acetamide herbicidal compound,
about 1 to about 100 parts of a chloroacetanilide herbicidal compound,
about 3 to about 400 parts of a thiolcarbamate herbicidal compound,
about 0.5 to about 100 parts of an azole herbicidal compound,
about 0.005 to about 20 parts of a pyrimidine herbicidal compound,
about 0.02 to about 60 parts of a sulphonylurea herbicidal compound,
about 3 to about 200 parts of a pyrazole herbicidal compound,
about 7.5 to about 400 parts of a propionanilide herbicidal compound,
about 0.2 to about 60 of a phenoxypropionic acid ester herbicidal compound,
about 1 to about 400 parts of a benzylurea herbicidal compound,
about 0.2 to about 100 parts of phenoxycarboxylic acid herbicidal compound, and
about 0.05 to about 120 parts of a triazine herbicidal compound or a weighted mixture thereof.

9. The method according to claim 5, wherein in addition to (A) one part by weight of the sulphonylaminophenyluracil, there is also applied (B) a synergistically effective amount of at least one of
about 20 to about 150 parts of an acetamide herbicidal compound,
about 5 to about 50 parts of a chloroacetanilide herbicidal compound,
about 5 to about 300 parts of a thiolcarbamate herbicidal compound,
about 2 to about 80 parts of an azole herbicidal compound,
about 0.1 to about 10 parts of a pyrimidine herbicidal compound,
about 0.03 to about 30 parts of a sulphonylurea herbicidal compound,
about 4 to about 120 parts of a pyrazole herbicidal compound,
about 10 to about 320 parts of a propionanilide herbicidal compound,
about 0.3 to about 40 of a phenoxypropionic acid ester herbicidal compound,
about 3 to about 300 parts of a benzylurea herbicidal compound,
about 1 to about 80 parts of a phenoxycarboxylic acid compound, and
about 0.1 to about 100 parts of a triazine herbicidal compound, or a weighted mixture thereof.

10. A herbicidal composition comprising:

(A) at least one sulphonyl phenyl aminouracil of the formula (Ia):

$$\text{(Ia)}$$

(chemical structure of formula Ia showing a pyrimidine-dione ring with H3C, CF3, N-CH3 substituents connected via N to a phenyl ring bearing F, CN, and NHSO2R2 groups)

wherein
R² represents methyl or ethyl; and (B) a synergistically effective amount of at least one herbicide compound selected from the group consisting of an acetamide herbicide, a chloroacetanilide herbicide, a thiolcarbamate herbicide, an azole herbicide, a pyrimidine herbicide, a sulphonylurea herbicide, a pyrazole herbicide, a propionanilide herbicide, a phenoxypropionic acid ester herbicide, a benzylurea herbicide, a phenoxycarboxylic acid herbicide and a triazine herbicide.

11. A herbicidal composition according to claim 10, wherein (A) comprises one part by weight of the sulphonylaminophenyluracil of the formula (a) and (B) comprises a synergistically effective amount of at least one herbicidal compound selected from the group consisting of 2-benzothiazol-2-yloxy-N-methylacetanilide, (RS)-2-bromo-N-(α,α-dimethylbenzyl)-3,3-dimethylbutylamide, 2-chloro-2',6'-diethyl-N-(2-propoxyethyl)acetanilide, 2-chloro-2',6'-diethyl-N-(butoxymethyl)acetanilide, 2-chloro-N-(3-methoxy-2-thienyl)-2',6'dimethylacetanilide, S-(4-chlorobenzyl)-N,N-dicthylthiocarbamate, S-benzyl-1,2-dimethylpropyl(ethyl)thiocarbamate, O-3-tert-butylphenyl 6-methoxy-2-pyridyl(methyl) thiocarbamate, S-ethylhexahyde-1H-azepin-1-carbothioate, 1-(diethylcarbamoyl)-3-(2,4,6-trimethylphenylsulfonyl)-1,2,4-thiazole, 1-(3-chloro-4-trifluoromethylphenyl)-4-(N,N-dimethylcarbamoyl)-5 (4H)-tetrazolinone, 1-(3-chloro-4-trifluoromethylthiophenyl)-4-(N,N-dipropylcarbamoyl)-5(4H)-tetrazolinone, 1-(3-chloro-4-trifluoromethoxyphenyl)-4-(N,N-dipropylcarbamoyl)-5(4H)-tetrazolinone,1-(3-chloro-4-isopropylphenyl)-4-(N,N-diethylcarbamoyl)-5(4H)-tetrazolinone, 1-(3-chloro-4-isopropylphenyl)-4-(N,N-dipropylcarbamoyl)-5(4H)-tetrazolinone, 1-(3chloro-4-isopropylphenyl)-4-(N,N-diallycarbamoyl)-5(4H)-tetrazolinone, 1-(2-chlorophenyl)-4-(N,N-dipropylcarbamoyl)-5(4H)-tetrazolinone, 1-(2-chlorophenyl)-4-N,N-dipropylcarbamoyl)-5(4H)-tetrazolinone, 1-(2-chloro-6-methylphenyl)-4-(N,N-diethylcarbamoyl)-5(4H)-tetrazolinone, 1-(2,6-dichlorophenyl)-4-(N,N-diethylcarbamoyl-5(4H)-tetrazolinone, 1-(2-chloro-6-methylphenyl)-4-(N-ethyl-N-isopropyl)-5(4H)-tetrazolinone, 1-(2-chloro-6-methylphenyl)-4-(N,N-dipropylcarbamoyl)-5(4H)-tetrazolinone, 1-(2-chlorophenyl)-4-(N-cyclopentyl-N-ethylcarbamoyl)-5(4H)-tetrazolinone, 1-(2-chlorophenyl)-4-(N-cyclopentyl-N-propylcarbamoyl)-5(4H)-tetrazolinone, 1-(2-chlorophenyl)-4-(N-cyclohexyl-N-ethylcarbamoyl)-5(4H)-tetrazolinone, 1-(2-chloro-6-methylphenyl)-4-(N-cyclopentyl-N-propylcarbamoyl)-5(4H)-tetrazolinone, 1-(2-bromophenyl)-4-N-(N-cyclopentyl-N-ethylcarbamoyl)-5(4H)-tetrazolinone, 1-(2-bromophenyl)-4-(N-cyclopentyl-N-propylcarbamoyl)-5(4H)-tetrazolinone, 1-(2-bromo-6-methylphenyl)-4-(N-cyclopentyl-N-propylcarbamoyl)-5(4H)-tetrazolinone, methyl 2[4,6-dimethoxy-2-pyrimidinyl)oxy]-6-[1-methoxyimino) ethyl]-benzoate, methyl α-(4,6-dimethoxypyrimidin-2-yl-carbamoylsulfamoyl)-O-toluate, ethyl 5-(4,6-dimethoxypyrimidin-2-yl-carbamoylsulfamoyl)-1-methylpyrazol-4-carboxylate, N-(2-chloroimidazole[1,2-a]pyridin-3-yl-sulfonyl)-N'-(4,6-dimethoxy-2-pyrimidinyl)urea, N-(4,6-dimethoxypyrimidin-2-yl) aminocarbonyl)-1-methyl-4-(2-methyl-2H-tetrazole-5yl)-1H-pyrazol-5-sulfonamide, N-[[4,6-dimethoxy-1,3,5-triazine-2-yl)amino]carbonyl]-2-(2-methoxyethoxy)benzenesulfonamide, 1-[[o-cyclopropylcarbonyl)phenyl]sulfamoyl-3-(4,6-dimethoxy-2-pyrimidinyl)urea, 4-(2,4-dichlorobenzoyl)-1,3-dimethylpyrazol-5-yl-p-toluenesulfonate, 2-[4-(2,4-dichloro-m-toluoyl)-1,3-dimethylpyrazol-5-yloxy]-4-methylacetophenone, 2-[4-(2,4-dichlorobenzoyl)-1,3-dimethylpyrazol-5-yloxy]acetophenone, 2-(β-naphthyloxy) propionanilide, (RS)-2-(2,4-dichloro-m-tolyloxy) propionanilide, n-butyl(R)-2-[4-(2-fluoro-4-cyanophenoxy)phenoxy]propionate, 1-(α,α-dimethylbenzyl)-3-p-tolylurea, N-[(2-chlorophenyl)methyl]-N'-(1-methyl-1-phenylethyl)urea, 2-methyl-4-chlorophenoxybutyric acid, 2,4-dichlorophenoxyacetic acid, 2,4-bis(ethylamino)-6-methylthio-1,3,5-triazine and 2-ethylamino-4-(1,2-dimethylpropylamino)-6-methylthio-1,3,5-triazine.

12. A herbicidal composition according to claim 10, wherein (A) comprises one part by weight of the sulphonylaminophenyluracil of the formula (Ia)

(B) comprises one part by weight of the sulphonylaminophenyluracil of the formula (I) of
about 20 to about 150 parts of an acetamide herbicidal compound,
about 5 to about 50 parts of a chloroacetanilide herbicidal compound,
about 5 to about 300 parts of a thiolcarbamate herbicidal compound,
about 2 to about 80 parts of an azole herbicidal compound,
about 0.1 to about 10 parts of a pyrimidine herbicidal compound,
about 0.03 to about 30 parts of a sulphonylurea herbicidal compound,
about 4 to about 120 parts of a pyrazole herbicidal compound,
about 10 to about 320 parts of a propionanilide herbicidal compound,
about 0.3 to about 40 of a phenoxypropionic acid ester herbicidal compound,
about 3 to about 300 parts of a benzylurea herbicidal compound,
about 1 to about 80 parts of a phenoxycarboxylic acid compound, and
about 0.1 to about 100 parts of a triazine herbicidal compound, or a weighted mixture thereof.

13. A herbicidal composition according to claim 12, wherein (A) is 1-(4-cyano-2-fluoro-5-methylsulphonylaminophenyl)-3,6-dihydro-2,6-dioxo-3,5-dimethyl-4-trifluoromethyl-1(2H)-pyrimidine.

* * * * *

UNITED STATES PATENT AND TRADEMARK OFFICE
CERTIFICATE OF CORRECTION

PATENT NO. : 5,641,725
DATED : June 24, 1997
INVENTOR(S) : Goto, et al.

It is certified that error appears in the above-indentified patent and that said Letters Patent is hereby corrected as shown below:

Col. 17, line 24   Delete " (a) " and substitute -- (Ia) --

Col. 17, line 50   Delete " dipropylcarbamoyl " and substitute -- diethylcarbamoyl --

Col. 18, line 35   After " (Ia) " insert -- and

Signed and Sealed this

Thirteenth Day of January, 1998

Attest:

BRUCE LEHMAN

Attesting Officer

Commissioner of Patents and Trademarks